United States Patent
Van Der Zwaag et al.

(10) Patent No.: US 9,194,972 B2
(45) Date of Patent: Nov. 24, 2015

(54) METHOD OF ADJUSTING PROPERTIES OF DRILLING FLUIDS AND APPARATUS FOR USE IN SUCH METHODS

(75) Inventors: Claas Van Der Zwaag, Stavanger (NO); Arild Saasen, Lier (NO); Tor Henry Omland, Stavanger (NO); Per Amund Amundsen, Stavanger (NO)

(73) Assignee: STATOIL PETROLEUM AS, Stavanger (NO)

( * ) Notice: Subject to any disclaimer, the term of this patent is extended or adjusted under 35 U.S.C. 154(b) by 977 days.

(21) Appl. No.: 13/254,426

(22) PCT Filed: Mar. 2, 2010

(86) PCT No.: PCT/GB2010/050361
§ 371 (c)(1),
(2), (4) Date: Oct. 7, 2011

(87) PCT Pub. No.: WO2010/116160
PCT Pub. Date: Oct. 14, 2010

(65) Prior Publication Data
US 2012/0013335 A1    Jan. 19, 2012

(30) Foreign Application Priority Data

Mar. 2, 2009   (GB) .................................. 0903580.9
Feb. 4, 2010   (GB) .................................. 1001833.1

(51) Int. Cl.
*G01V 3/32*    (2006.01)
*G01N 24/08*   (2006.01)

(52) U.S. Cl.
CPC  *G01V 3/32* (2013.01); *G01N 24/08* (2013.01); *G01N 24/081* (2013.01)

(58) Field of Classification Search
CPC ........ G01V 3/32; G01N 24/08; G01N 24/081
USPC .......................... 324/300–322; 600/409–445
See application file for complete search history.

(56) References Cited

U.S. PATENT DOCUMENTS

| | | | |
|---|---|---|---|
| 3,508,438 A | 4/1970 | Alger et al. | |
| 4,171,642 A | 10/1979 | Taylor | |
| 4,412,179 A * | 10/1983 | Brown | ......................... 324/303 |

(Continued)

FOREIGN PATENT DOCUMENTS

| | | |
|---|---|---|
| CA | 2 450 598 A1 | 6/2004 |
| DE | 4119711 A1 | 12/1992 |

(Continued)

OTHER PUBLICATIONS

D'Avila et al., "Magnetic Resonance Imaging (MRI): A Technique to Study Flow an Microstructure of Concentrated Emulsions", Brazilian Journal of Chemical Engineering, vol. 22, pp. 49-60, Jan.-Mar., 2005, Brazil.

(Continued)

*Primary Examiner* — Dixomara Vargas
(74) *Attorney, Agent, or Firm* — Birch, Stewart, Kolasch & Birch, LLP.

(57) ABSTRACT

The present invention provides a method of determining a physiochemical property of a drilling fluid at a drilling site during a drilling phase, said method comprising detecting a nuclear magnetic resonance signal from out-of-hole drilling fluid at said site and calculating therefrom a value indicative of said property.

24 Claims, 5 Drawing Sheets

(56) References Cited

U.S. PATENT DOCUMENTS

| | | |
|---|---|---|
| 4,710,713 A | 12/1987 | Strikman |
| 4,733,233 A | 3/1988 | Grosso et al. |
| 4,785,245 A | 11/1988 | Lew et al. |
| 4,901,018 A | 2/1990 | Lew |
| 4,933,638 A | 6/1990 | Kleinberg et al. |
| 5,216,366 A | 6/1993 | Young |
| 5,306,640 A | 4/1994 | Vinegar et al. |
| 5,565,775 A | 10/1996 | Stallmach et al. |
| 5,684,399 A | 11/1997 | Bayer |
| 6,046,587 A | 4/2000 | King et al. |
| 6,107,796 A | 8/2000 | Prammer |
| 6,111,408 A * | 8/2000 | Blades et al. ............... 324/303 |
| 6,111,409 A | 8/2000 | Edwards et al. |
| 6,140,817 A | 10/2000 | Flaum et al. |
| 6,577,125 B2 * | 6/2003 | Prammer et al. ............. 324/303 |
| 6,661,226 B1 * | 12/2003 | Hou et al. .................... 324/303 |
| 6,794,864 B2 | 9/2004 | Mirotchnik et al. |
| 6,803,761 B2 * | 10/2004 | Prammer et al. ............. 324/303 |
| 6,815,950 B2 * | 11/2004 | Speier .......................... 324/303 |
| 6,825,657 B2 | 11/2004 | Kleinberg et al. |
| 7,053,611 B2 | 5/2006 | Freedman |
| 7,164,267 B2 | 1/2007 | Prammer et al. |
| 7,495,436 B2 * | 2/2009 | Hamdan et al. ............. 324/303 |
| 8,093,893 B2 * | 1/2012 | Niemeyer et al. ........... 324/303 |
| 8,427,145 B2 * | 4/2013 | Mitchell et al. ............. 324/303 |
| 8,610,431 B2 * | 12/2013 | Chen et al. .................. 324/303 |
| 8,686,724 B2 * | 4/2014 | Mitchell et al. ............. 324/303 |
| 2002/0140425 A1 | 10/2002 | Prammer et al. |
| 2005/0028973 A1 | 2/2005 | Paluch et al. |
| 2005/0221495 A1 | 10/2005 | Bell et al. |
| 2006/0071661 A1 | 4/2006 | Ong |
| 2006/0097722 A1 | 5/2006 | Scheven |
| 2006/0213283 A1 | 9/2006 | Morris et al. |
| 2006/0272812 A1 | 12/2006 | Yu et al. |
| 2007/0029113 A1 | 2/2007 | Chen |
| 2007/0114996 A1 | 5/2007 | Edwards |
| 2008/0036457 A1 * | 2/2008 | Thern et al. .................. 324/303 |
| 2009/0125239 A1 * | 5/2009 | Niemeyer et al. ............. 702/11 |
| 2009/0260430 A1 | 10/2009 | Zamfes |

FOREIGN PATENT DOCUMENTS

| | | |
|---|---|---|
| EP | 0 347 180 A2 | 12/1989 |
| EP | 0496330 A2 | 7/1992 |
| EP | 0 581 666 A3 | 2/1994 |
| EP | 1457778 A1 | 9/2004 |
| FR | 2864241 A1 | 6/2005 |
| GB | 2 336 213 A | 10/1999 |
| GB | 2 341 685 A | 3/2000 |
| GB | 2 367 130 A | 3/2002 |
| GB | 2 433 273 A | 6/2007 |
| RU | 2 152 006 C1 | 6/2000 |
| WO | WO 99/54747 | 10/1999 |
| WO | WO 02/14907 A1 | 2/2002 |
| WO | WO 03/087861 A1 | 10/2003 |
| WO | WO 2005/067569 A3 | 7/2005 |
| WO | WO 2009/142840 A2 | 11/2009 |
| WO | WO 2010/039121 A1 | 4/2010 |

OTHER PUBLICATIONS

International Search Report from PCT/GB2010/050361, dated Aug. 3, 2010. 1—.

Martignoni et al., "Evaluation of Cyclone Geometry and Its Influence on Performance Parameters by Computational Fluid Dynmaics (CFD)", Brazilian Journalist of Chemical Engineering, vol. 24, No. 1, pp. 83-94, Jan.-Mar. 2007, Brazil.

Rismanto et al., "Explorative Study of NMR Drilling Fluids Measurement" -Annual Transactions of the Nordic Rheology Society, vol. 15, 2007, Stavanger, Norway.

* cited by examiner

METHOD OF ADJUSTING PROPERTIES OF DRILLING FLUIDS AND APPARATUS FOR USE IN SUCH METHODS

This invention relates to improvements in and relating to the out-of-hole monitoring of physiochemical properties of drilling fluids, in particular methods of determining properties of drilling fluids, methods of adjusting properties of drilling fluids, and apparatus for use in such methods.

BACKGROUND

When boreholes are drilled into subterranean reservoirs, e.g. hydrocarbon reservoirs, the drill bit during drilling is conventionally surrounded by a drilling fluid which is continuously pumped down to the distal end of the borehole and back to the drilling head, e.g. down through the hollow drill string which carries the drill bit and back through the annulus between the drill string and the inner wall of the borehole. The circuit from drill head down hole and back to the drill head may take the drilling fluid several hours to complete.

One of the functions of the drilling fluid is to carry the debris and cuttings created by drilling out of the borehole and accordingly, on reaching the drill head, the drilling fluid is generally screened to remove debris before being returned to a holding tank, generally referred to as a drilling fluid reservoir, from which it can be recycled down hole. It is important that debris and cuttings are removed efficiently from the wellbore because they can interfere with the operation of the drill bit and can significantly impede the progress of the drilling operation.

In terms of other functions, the drilling fluid pumped into a wellbore also helps to drive the drill bit into the wellbore and to cool and lubricate the drill bit. Further, it may be applied to counterbalance hydrostatic pressure in the wellbore thereby preventing blow out. The drilling fluid also functions to maintain borehole stability by generating a pressure against the wellbore wall and thereby prevent it from collapsing. It also provides fluid loss control, i.e. it prevents loss of fluid into the formation, and it provides chemical stability to the formation thereby preventing chemically induced instability of the wellbore.

These functions should ideally be achieved whilst minimising formation damage and thus the subsequent impairment of the production from a well or the ability to inject fluids such as gas or water for production support into the well. Damage may be caused by solid particles contained in the drilling fluids or drilling fluids filtrate that enter the formation. These drilling fluids components may trigger reactions such as plugging of flow paths through said solid particles, the mobilization of fine particles, the swelling of clay minerals, changes in fluids saturations, the generation of stable emulsion droplets, and the precipitation of organic or inorganic scale. Each of these reactions has the potential to reduce the effective permeability of the formations that are entered by the wellbore either for production of the formation contents or injection of gas or water.

The particular composition of the drilling fluid can impact significantly on its ability to perform these various functions whilst minimising formation damage. At the same time, downhole conditions such as wellbore mineralogy, temperature and pressure, drilling rates and trajectory, well length and volume etc, can affect fluid effectiveness. It is clearly desirable to use a drilling fluid that is suitable for given downhole conditions and achieves one and ideally all of the functions above.

Drilling fluids are typically water or oil based compositions comprising a mixture of chemicals designed to achieve the above-described range of functions. Drilling fluids are discussed for example in Darley and Gray "Composition and Properties of Drilling and Completion Fluids", Gulf Professional Publishing, $5^{th}$ ed., 1988. Fluids may be formed, for example, with certain viscosities, densities, fluid loss control properties and chemical contents in order to try to provide the desired performance. However, well and wellbore conditions continuously change during the performance of a wellbore operation as, for example, drilling progresses and different geological intervals are entered. Cuttings and debris from the formation may also become mixed into and suspended in the fluid and re-circulated back into the borehole if they are not effectively removed at the surface.

Drilling fluids are complex chemical mixtures designed to achieve a variety of tasks and in use their performance can worsen as their physiochemical properties alter. Drilling fluids in motion experience mechanical wear through the drilling and pumping process that causes the degradation or deterioration of drilling fluid components. Also, the interaction between the drilling fluid and subterranean formation causes the removal or degradation of drilling fluid components by the formation due to reactions between formation and fluid. As components disappear, degrade or deteriorate, they cannot efficiently maintain the physiochemical properties of the fluid and have to be replaced by new components. Wellbore pressure and temperature impact on the fluid as well as the nature of the formation. Accordingly the properties, e.g. viscosity, of the drilling fluid may change significantly during the drilling operation affecting its subsequent performance when it is recirculated back into a wellbore.

As a result, it can be difficult for operators to select an appropriate drilling fluid for an operation and once a particular fluid is chosen by an operator, it is uncertain whether it is going to continue to be an appropriate drilling fluid once subjected to the wellbore environment. As a result, the productivity of the drilling operation can be detrimentally affected. It is thus conventional for samples of returning drilling fluid to be taken and subjected to a battery of tests to determine values for its properties. Based on the results from those tests, the drilling fluid may be treated, e.g. by the addition of various components, so as to bring the values of these physiochemical properties back into the appropriate ranges for recycling down hole.

Examples of the physiochemical properties that are currently measured include: mud weight, viscosity, gel strength, water content, oil content, oil/water ratio, solids content, sand content, barite content, pH, methylene blue capacity, filtrate alkalinity, mud alkalinity, salt content, chloride content, potassium content, lime content, barite sag stability, etc. Some of these properties are time-invariant; however others are kinetic in that a measurable property develops over time in a static or agitated sample. Thus for example drilling fluid at rest develops a gel-like consistency which is broken when the fluid is agitated. Similarly, aged drilling fluid at rest has a tendency to "sag"; the high density solids such as barite, added to increase the pressure at the drilling site, develop an undesirable tendency to settle out.

This subjection to a battery of tests and the subsequent manual adjustment of the drilling fluid is, however, time consuming and labour intensive and does not allow for rapid intervention if a sudden change in properties occurs.

We have found that this problem may be addressed by monitoring physiochemical properties of the drilling fluid using nuclear magnetic resonance (NMR), in particular low field NMR. Advantageously this enables the physiochemical properties of the drilling fluid to be monitored during the drilling phase and if necessary for rapid intervention to be carried out to ensure that the properties of the drilling fluid are optimised.

NMR has previously been used in down-hole monitoring of liquids entering the borehole from the surrounding matrix, i.e. during a production or completion phase. This is, for example, disclosed in US2008/0035332 wherein NMR is one of the methods used to take measurements on reservoir fluids pumped into the flowline of a fluid sampling tool. The use of NMR has not, however, previously been disclosed for on-line monitoring of out-of-hole drilling fluids during a drilling phase.

SUMMARY OF INVENTION

Thus viewed from one aspect the invention provides a method of determining a physiochemical property of a drilling fluid at a drilling site during a drilling phase, said method comprising detecting a nuclear magnetic resonance signal from out-of-hole drilling fluid at said site and calculating therefrom a value indicative of said property.

Viewed from a further aspect the invention provides a process for controlling the physiochemical properties of a drilling fluid comprising determining said properties using the method of the invention, comparing the determined properties with pre-set target values for said properties, and modifying the drilling fluid (e.g. adding material to the drilling fluid) to adjust said properties towards said target values.

Viewed from a further aspect the invention provides apparatus for determining properties of out-of-hole drilling fluid, said apparatus comprising: a drilling fluid flow tube, optionally valved to stop fluid flow therethrough, the walls of at least a portion of said tube being of a non-magnetic material; disposed at said portion a nuclear magnetic resonance apparatus; and a computer arranged to receive signals from said apparatus indicative of nuclear magnetic resonance parameters of fluid in said tube and to calculate therefrom values for said properties of said fluid.

By non-magnetic in this context is meant not ferromagnetic or ferrimagnetic, e.g. not of iron or iron alloys.

Viewed from a further aspect the invention provides a drilling fluid reservoir having mounted therein a nuclear magnetic resonance apparatus.

DESCRIPTION

Drilling fluid is sometimes referred to as drilling mud. Drilling fluids are also sometimes referred to in the art as being gel forming. As used herein, the term drilling fluid encompasses drilling muds and drilling fluids capable of forming gels. The drilling fluid is preferably used to suspend and transport cuttings and/or debris produced during drilling out of the wellbore.

In preferred drilling operations the drilling fluid provided to the wellbore is recirculated, preferably recirculated continuously, during the drilling phase. Thus preferably the drilling fluid is provided to the wellbore, it is produced therefrom, optionally purified (e.g. filtered) and reintroduced into the wellbore. Drilling operations based on such recirculation techniques are advantageous as they are cost efficient compared to techniques using only fresh supplies of drilling fluids. The typical drawback of recirculating drilling fluid is that its properties may change during use and no longer be ideal for the purpose it is supposed to serve. A major advantage of the present invention is that it enables the properties of the drilling fluid to be regularly or continuously monitored and if necessary regularly or continuously adjusted or modified to ensure the characteristics of the drilling fluid are optimised even when recirculated.

An important feature of the present invention is that a physiochemical property is detected and calculated at a drilling site during a drilling phase. Thus at least one physiochemical property of the drilling fluid is calculated whilst the drilling operation is ongoing (i.e. drilling is not stopped). Preferably therefore the steps of detecting a NMR signal from the drilling fluid and the calculating of the fluid property therefrom is in real time. This is in contrast to methods wherein a sample of drilling fluid is taken and a measurement is taken at some later point in time, e.g. after the fluid has been transported to a laboratory. The present invention therefore enables rapid interventions to change or modify a drilling fluid to occur.

Thus in preferred methods and processes of the present invention the steps of detecting a NMR signal from drilling fluid and calculating a physiochemical property of the fluid occurs at intervals, e.g. regular, intervals during the drilling phase. The interval may be, for example, 30 seconds-2 hours, preferably 1 minute-1.5 hour, more preferably 5 minutes-1 hours, still preferably 10 minutes-45 minutes, more preferably 15 minutes-40 minutes or about 15-20 minutes depending, for example, on the property being measured and the NMR technique and set up being used. Preferably, however, the interval is less than 60 minutes, still more preferably less than 45 minutes, e.g. 10 to 30 minutes. In methods and processes of the invention wherein determining a physiochemical property of the drilling fluid comprises measuring more than one property of the fluid, the interval between measurements of the properties may be the same or different depending on the equipment, technique and configuration being used.

Particularly preferably the steps of detecting a NMR signal from drilling fluid and the calculating a physiochemical property of the fluid therefrom occurs substantially continuously (e.g. continuously) during the drilling phase. To enable this, the steps are preferably automated.

By out-of-hole, it is meant herein that the monitoring is of the drilling fluid before it enters the borehole, or after it has left the bore-hole. Conventional down-hole monitoring with NMR is generally of fluids entering the borehole from the surrounding formation, and any drilling fluid that may be present is essentially a contaminant. In contrast the methods, processes and apparatus of the present invention are specifically designed to determine properties of drilling fluid outside of the wellbore. Thus the fluid tested preferably comprises at least 95% drilling fluid, more preferably at least 99% drilling fluid. Still more preferably the sample tested consists of drilling fluid.

In the present invention, the NMR signal may be detected from drilling fluid passing from the borehole to the drilling fluid reservoir, from drilling fluid in the fluid reservoir, or from drilling fluid passing from the fluid reservoir to the borehole, or in any such case from a sample extracted from such flow or the reservoir. Preferably the NMR signal is at least detected from drilling fluid passing from the fluid reservoir to the borehole.

Likewise the NMR signal may be detected for two or more (e.g. three) locations along the out-of-hole flow path from borehole back to borehole and/or at two or more time points for any such sample. Preferably the NMR signal is detected in the drilling fluid reservoir and in the out-of-hole flow path from the borehole to the drilling fluid reservoir and/or in the path from the fluid reservoir to the borehole. The former assesses the progress of treatment whilst the out-of-hole flow path measurements assess the affect of the formation and drilling operation on the drilling fluid and the results of modifications made to the drilling fluid in the fluid reservoir respectively.

Thus convenient locations for the NMR signal detector are on a flowline for the drilling fluid, on a bypass-line (e.g. on a sampling and returning bypass-line of a flowline for drilling fluids), on a sampling side line (e.g. from a flow line for drilling fluids), in the drilling fluid reservoir, and on a position suitable for receiving a sample taken from a flowline, bypass-lines, side line or the reservoir. Preferably the NMR signal detector is on a bypass-line or a flowline, especially a bypass-line, which facilies the measurement of time variant and time invariant properties. Preferably the NMR signal detector is on a flowline or bypass line for drilling fluid returning from the borehole to the drilling fluid reservoir. Preferably the NMR signal detector is on a flowline or bypass line for drilling fluid being pumped from the drilling fluid reservoir into the borehole.

The NMR signal detector may be any NMR apparatus capable of causing the drilling fluid to emit a detectable NMR signal and capable of detecting that signal. In general this will comprise a magnet, a radiofrequency detector and a radiofrequency emitter.

The apparatus may also be provided with radiofrequency coils that impose spatially dependent, static or pulsed magnetic field gradients in any direction, strength, shape or duration.

The magnet may have any of the formats conventional in NMR and MRI apparatus, e.g. hollow cylindrical or open (e.g. horseshoe), and the magnetic field may be permanent or may be created by an electric current, e.g. in superconducting or non-superconducting coils. The use of open magnets is especially preferred as they may readily be positioned at desired locations along a line or conduit so as to detect signals from drilling fluid within the line or conduit and may be repositioned without need to halt flow within the line/conduit and disassemble the line/conduit. The signal detector will typically be a magnetic resonance imager or an NMR apparatus capable of detecting a relaxation time dependent signal or a radio frequency dependent signal, either in one spatial dimension or spatially resolved (two- or three-dimensional), such as an NMR-spectrometer or a magnetic resonance imager.

The NMR parameters that are measured will preferably be the hydrogen ($^1$H) proton spin relaxation times, i.e. $T_1$, $T_2$ and $T_2^*$, signal amplitudes/intensities, and the translational diffusion coefficient (D), although chemical shift and peak broadening may also be measured. Preferably the NMR parameter measured is a hydrogen proton spin relaxation time, especially $T_2$. Preferably these parameters are measured using spin relaxation time measurements and/or in pulsed gradient spin echo measurements. Examples of suitable spin relaxation time measurement methods are given in Coates G. R., Xiao L. and Prammer M. G. (1999) "NMR Logging—Principles and Applications", Halliburton Energy Services Publication H02308 and examples of suitable pulsed gradient spin echo measurements are summarized by Johns M. L. and Hollingworth K. G. (2007) "Characterization of Emulsion Systems", Nuclear Magentic Resonance Spectroscopy, 50, pages 51-70.

The NMR apparatus will be set up in configurations known to the skilled man depending on, for example, the NMR measurement technique being used, the NMR parameter being detected and the drilling fluid property being calculated. The NMR-apparatus will require frequent shimming/tuning and calibration. The skilled man is able to carry out shimming, tuning and calibration as required.

Generally calibration will be performed on samples of water, brine and/or oil. These samples may be included in a reservoir provided in the instrument setup. A dedicated calibration routine will typically be used, as is the case with conventional NMR apparatus. A cleaning routine is preferably run before any calibration and between measurements.

In the methods and processes of the invention the $^1$H of water is preferably detected. Where the drilling fluid contains important compounds with characteristic $^1$H-NMR peaks, for example glycol, the relaxation times, intensities, shifts, etc of these too may be measured. The NMR signals from more "exotic" nuclei than $^1$H may of course also be measured if this is deemed to be desirable. Representative examples of other nuclei that may be detected are $^{13}$C, $^{31}$P, $^{19}$F and $^{33}$S. For some properties, e.g. flow rate, it may be desirable to use a pulsed radiofrequency source and to measure the integrated detected free induction decay signal (i.e. the peak area).

In the present invention the physiochemical property of the drilling fluid determined may be any physical or chemical property of the fluid. The property may be a time invariant property or a time variant property. As used herein a time invariant property is a property that does not vary over time. These properties may therefore be determined at any given instant and the measurement is generally representative of the property. In contrast a time variant property is a property that varies with time. Time variant properties may also be described as kinetic properties. With time variant properties, it is generally preferable to make several determinations of the given property over a time period.

Preferably the physiochemical property determined is selected from the group consisting of:

Viscosity,
Density,
Fluid loss control properties;
Acidity;
$H_2S$ content;
Solids content, e.g. sand and/or barite content,
Gel strength,
Time to build up gel strength,
Emulsion droplet size,
Emulsion stability,
Particle and fluid segregation processes (sag),
Oil:water ratio,
Oil:brine ratio,
Oil content,
Water content,
Brine content,
Dissolved gas content;
Glycol content.

More preferably the physiochemical property determined is selected from the group consisting of:

Viscosity
Oil:water ratio or oil:brine ratio,
Emulsion droplet size,
Time to build up gel strength,
Particle and fluids segregation processes (sag),
Dissolved gas content.

Preferably the physiochemical property determined is selected from the group consisting of oil content, emulsion stability, emulsion droplet size, particle and fluids segregation, especially sag, and dissolved gas content.

The table below shows which properties are considered herein to be time variant and time invariant.

| Time variant | Time invariant |
|---|---|
| Gel strength | Viscosity |
| Time to build up gel strength | Density |
| Particle and fluids segregation processes | Solids content |
| Emulsion droplet size | Fluid loss control |
| Emulsion stability | $H_2S$ content |
| Dissolved gas content | Acidity |
| | Oil content |
| | Water content |
| | Brine content |
| | Oil:water ratio |
| | Oil:brine ratio |
| | Glycol content |

Where a time-variant property of the drilling fluid, e.g. gelling or segregation (e.g. sag), is to be measured, this can be done on a non-flowing sample, e.g. a sample taken from the drilling fluid flow or more preferably a sample in a bypass flowline in which flow has been stopped. Alternatively, the flow may be allowed to continue but the flowline may be so shaped as to cause the drilling fluid to become non-uniform, e.g. the fluid may be subjected to gravity or a centrifugal force perpendicular to the overall flow direction, for example by being given a rotary motion in the plane perpendicular to that direction. Where this is done, the radially outer portion of the fluid will become denser than the radially inner portion. The difference in the NMR signals from outer and inner portions thus can be correlated to the sag of the fluid. Such different signals may be recorded by separating inner and outer portions, e.g. using a cyclone with an axial exit and a peripheral exit, or by placing NMR apparatus to either side of the flowline, e.g. within and outside a helical section of the flowline. In both cases flow need not be stopped.

In the present invention, at least one physiochemical property of the drilling fluid is determined. Preferably two or more, e.g. 3, 4, 5 or 6 physiochemical properties of the drilling fluid are determined during an operation.

Correlation between the NMR measurements and the properties of the drilling fluid (e.g. viscosity, drilling solids/fines content, gel strength, time to build up gel strength, emulsion droplet size, emulsion stability, sag, oil:water ratio (or oil or water or brine content), dissolved gas, glycol (or other dissolved component) content, etc.) may readily be achieved by comparison with standards, i.e. samples having a range of values of these properties as measured by other means. Thus, for example, sag correlates well with proton signal amplitude.

Nonetheless it will be particularly efficient to measure the NMR parameters for a large range of standards and then, using multivariate analysis, to generate a prediction matrix which, when applied to the measured NMR parameters for the "unknown" sample, itself generates values for the desired parameters of the unknown sample.

Such generated values may of course be quantitative, semi-quantitative, or qualitative, e.g. for temperature: 72° C.; between 70 and 75° C.; below 100° C.; "too hot"; or "satisfactory".

To differentiate between different drilling fluid properties, the method of NMR measurement and/or the measured data values may be manipulated to extract the correct correlation. In other words different NMR measurement techniques may be used to measure a NMR parameter in more than one way. Thus for example, different $T_1$ or $T_2$ measurement techniques may be used (for example $T_2$-free induction decay and CPMG (Carr, Purcell, Meiboom, Gill) spin echo sequence). By measuring $T_2$ by different techniques, more than one drilling fluid property (e.g. two) may be correlated with the data. Moreover by manipulating the $T_2$ data in different ways, yet further drilling fluid properties may be extracted. Thus, for example, $T_2$ may be determined by a free induction decay and the $T_2$ values correlated with oil content and the signal amplitude correlated with sag.

Alternatively, or additionally, different set-up parameters, such as magnetization, echo-spacing or pulse gradient direction, shape and strength may be used. In other words the configuration of the NMR apparatus may be varied. This also enables the same NMR parameter to be correlated with more than one drilling fluid property. Thus with signals measured by two or more NMR measurement techniques and/or different set up configurations, evaluation algorithms may then be used to calculate the value of the desired drilling fluid property.

When operators are initially deciding which drilling fluid to use in a particular drilling phase, they will typically have an "ideal" fluid specification in mind. Thus for each drilling fluid characteristic (e.g. viscosity, density, acidity etc) there will exist a pre set value or range within which they would like that property of the fluid used to fall. Operators may develop this specification, for example, as a result of prior experience of performing the drilling operation, or similar operations, or derive it from laboratory testing.

An example specification for a water-based drilling fluid might be:
Viscosity: Shear stress of 80-100 lb/100 ft$^2$ at 1021 s$^{-1}$
Density: 1450 kg/m$^3$
Oil/water ratio: 78/22-82/18
Emulsion stability: >500 mvolt
Particle size distribution: $d_{90}$ 280-350 µm
Solids content: 20-25 vol %

Thus preferred methods and processes of the invention, further comprise the step of comparing the determined physiochemical property with a pre-set value or range for said property. Typically fluid properties in a specification are specified at standard conditions, e.g. ambient temperature, such as 20° C., and pressure. The standard conditions may vary between different fluid properties. Hence in come cases the conditions under which the NMR detection takes place may need to be taken into account when comparing the determined property with the pre set value or range. This is generally straightforward and may, for instance, be achieved by applying a factor taking into account, e.g. the temperature and pressure at which is the measurement is made.

Thus once a physiochemical property of the drilling fluid is measured during the drilling phase, it is compared against the pre-set value or range. This assessment step may be carried out by the equipment used to perform the measurement. More preferably the assessment step may be carried out by a computer arranged to receive signals (i.e. data) from the NMR apparatus. In instances where the assessment is that the drilling fluid property falls inside the pre-set value or range, there is no need to modify the drilling fluid provided to the wellbore. On the other hand, when the assessment is that the drilling fluid does not fall inside the pre-set value or range, the drilling fluid is preferably modified. Preferably the modification adjusts the property towards the target value. Preferably the modified fluid has fluid properties inside the pre-set value or range.

In preferred methods and processes of the invention the step of modifying the drilling fluid is carried out during the drilling phase. This is highly advantageous as it means that the drilling fluid provided to the wellbore is optimised (i.e. is within the pre set values) throughout the drilling phase regardless of, for example, changes in the well or wellbore conditions and the presence of cuttings in the fluid. This enables rapid intervention to counteract, for example, the affects of chemical reactions between the drilling fluid and the formation and loss of fluid or components of the fluid to the formation.

Using the methods and processes of the invention, especially continuously or periodically and especially preferably in an automated mode, abnormalities in the drilling fluid may be picked up and rapidly compensated for. Such compensation may itself be automated. In particularly preferred methods of the present invention the steps of detecting, calculating, comparing and modifying are all automated.

Thus in particularly preferred methods and processes of the invention the step of modifying is carried out at (e.g. regular) intervals between 5 minutes-1 hour, e.g. intervals between 10 minutes-30 minutes during the performance of the drilling phase.

Still more preferably the step of modifying is carried out substantially continuously. This may be achieved, for example, when the step of modifying the drilling fluid is automated.

A preferred method, e.g. an automated method, of the present invention therefore comprises the steps of:
detecting a nuclear magnetic resonance signal from out-of-hole drilling fluid at said site;
calculating therefrom a value indicative of said property;
comparing the determined property with a pre-set value for said property; and
optionally modifying the drilling fluid provided during the drilling phase.

The step of modifying the drilling fluid provided to the wellbore in response to the calculated property may, for example, involve altering the proportions of the components of the drilling fluid, adding one or more additional components to the fluid or removing (e.g. stopping the supply of one or more components). Preferably the response is alteration of the proportions of the components of the fluid. In the process of the invention, the materials added or altered will typically be drilling fluid components, e.g. water, oil, emulsifiers, pH adjusters, weighting agents, etc.

Representative examples of modifications that may be made in response to various calculated properties are listed below:
Viscosity is too low: Amount of clay mineral increased or clay mineral added
Density is too low: Amount of weighting agent increased or weighting agent added
Acidity (pH) is too high: Amount of acid (e.g. citric acid) increased and/or amount of alkali decreased
Oil/water ratio is too high: Water (brine) content is increased
Emulsion stability is too low: Emulsifier, shear energy or specific solids e.g. clay minerals, are added In preferred methods of the invention, a fluid mixing model is used to determine the alteration necessary to modify the drilling fluid properties. Preferred fluid mixing models are therefore able to calculate the compositional change necessary to cause the necessary change in a fluid property, e.g. viscosity and density. The fluid mixing models may be prepared on the basis of tests carried out in the laboratory and/or prior work carried out in the formation. The man skilled in the art can readily generate suitable algorithms to function as the model. Multivariate models are preferred since they enable the simultaneous optimisation of a number of fluid characteristics.

The mixing model provides a "sensitivity map" of how chemical changes to drill fluids of different types and compositions control the fluid properties. In particular, the model may incorporate links in the form of specific correlations that describe the effect of a chemical additive on a characteristic of the fluid. For example, a polymer such as a xanthan polymer can be correlated to the viscosity of a water based mud. In such an example, the addition of xanthan polymer may have the following effect on 3 rpm and 600 rpm viscosimeter readings in the fluid: addition of 1 kg/m$^3$ increases 3 rpm by 1 and 600 rpm by 8. This relationship can be tabulated and programmed to form a "viscosity increasing" or "viscosifying" correlation in the mixing model.

To provide a further example, a correlation between the addition of a polymer and the fluid property of fluid loss control may be specified in the mixing model. Supposing a fluid property measurement for fluid loss is 8 ml, then addition of 3 kg/m$^3$ PAC ELV may reduce fluid loss by half (i.e. addition of 3 kg/m$^3$ gives fluid loss of 4 ml, addition of 6 kg/m$^3$ gives fluid loss of 2 ml). This relationship between quantity of PAC ELV additive and reduction fluid loss can similarly be tabulated and programmed into the mixing model so that the fluid can be modified by the appropriate addition of polymer to bring it within the required specification.

Accordingly, on being presented with the drilling fluid measurements, the mixing model can determine what additives require to be added, in what quantity and under what conditions in order to modify the drilling fluid such that it is brought within the specification. These additives includes both solid materials such as weighting materials e.g. in powder form, and fluid chemicals. Once this is determined, a corresponding control signal is sent to flow valves in an injection line to open them as required and add an additive to the fluid in the drilling fluid reservoir. The flow valves are remotely controllable and adjustable so that additives can be added at a certain flow rate.

In other embodiments, a premix may be used and added to the drilling fluid in order to modify it and bring it within the specification. Such a premix is a fluid mixture with constituent chemicals present in pre-determined proportions. It is a "ready made" additive that may have been tested and is known to provide a particular effect on a drilling fluid. In typical embodiments, the premix consists of a fluid blend of the chemicals normally present in a drilling fluid, but without weighting materials such as barite. The viscosity of the premix can be higher than the drilling fluid specification or lower, e.g. to increase or decrease the viscosity of the drill fluid. In this way, the premix can be applied in accordance with the mixing model to control properties such as viscosity and density of the drilling fluid, and at the same time control the chemical composition. Control of viscosity can for example be performed by adding a suitable amount of either high or low viscosity premix from a storage tank. Control of density may be performed by using a particular premix in combination with addition of dry weighting material such as barite to the fluid. Different types of premixes can be used, which may be prepared away from the fluid handling system and transported to the processing facility as required.

The methods and processes of the present invention therefore ensure that the drilling fluids provided to the wellbore are optimised for a significant proportion of the time the drilling phase runs. In particularly preferred methods wherein the steps are automated, the fluid may be optimised for the entirety of the drilling phase. This ensures that cuttings are removed efficiently so the wellbore is clean, the wellbore is stable, the wellbore is drilled efficiently and at the same time the formation is not damaged. The duration of a typical wellbore operation may be 12 hours-7 days, e.g. 24 hours-5 days.

The NMR apparatus used in the present invention may be any conventional apparatus; however where it is to be immersed in the drilling fluid it, and its power supply, should be provided with a fluid impermeable casing. Typically magnet strength will be in the range 1 to 100 MHz, preferably 2 to 20 MHz. (For NMR apparatus for $^1$H-NMR, the field strength is generally specified in terms of the applied radiofrequency since the proton signal frequency is directly proportional to the applied field strength. For MRI by contrast, the field strength is normally given in actual field strength units, e.g. Gauss or Tesla).

The apparatus of the present invention preferably comprises a flow tube. This may be the main flowline (i.e. the line through which the drilling fluid passes during circulation), a bypass line or a side line. Typically this will be a bypass line, although it can be the main flowline. Furthermore, as indicated earlier, the measurement may take place in the reservoir itself in which case no tube for the drilling fluid is needed. Nevertheless it may be appropriate to place an open ended vertical tube through the magnet (preferably a cylindrical magnet) in the reservoir to create an essentially static sample to allow time-variant properties such as sag or gel formation to be measured. Furthermore, where the NMR apparatus is in the reservoir it may be moved between different positions, generally vertically separated, to check for drilling fluid non-uniformities, e.g. to provide a measure of sag. The section of the flowline or tube at which NMR measurement is effected should be of a non-magnetic material, e.g. a non-magnetic metal (such as aluminium), glass, ceramic or plastics.

In the apparatus of the invention, the flow tube is conveniently mountable as part of, or more preferably, as a side line to, one of the flow tubes connecting the drilling fluid reservoir and the drill string or the drilling fluid discharge site at the top of the borehole. To this end it preferably has flanges for such attachment. In contrast, tools with NMR apparatus for downhole monitoring of liquids from the formation will tend to be open-ended and so will not be provided with such flanges so as to create a longer, closed, flow conduit.

The computer in the apparatus of the invention may be housed within the NMR apparatus. The computer may alternatively be in a control room at the drilling site or even remote therefrom and in any event is preferably arranged to communicate its calculated values to a control room. The calculated values may, as indicated earlier, be quantitative, semi-quantitative or qualitative. Preferably the computer also carries out the step of comparing the determined property to the pre set value or range as described above.

The apparatus of the invention may be provided with two or more NMR apparatuses arranged at the same or different locations along the flowline. The NMR apparatus may optionally be movable between different locations at or along the flowline.

The apparatus of the invention may if desired include further measuring instruments arranged to measure properties of the drilling fluid in the flow tube, e.g. temperature sensors, pH sensors, light absorbance, transmission or scattering sensors, mass sensors (i.e. density sensors), etc. Again these are preferably arranged to communicate detected values to the computer.

The apparatus of the invention may if desired also include the drilling fluid reservoir and the drilling fluid flowlines from reservoir to well head and well head to reservoir. The flow tube in the apparatus is preferably a part of a by-pass line or of one of these flowlines.

As mentioned earlier, in an alternative format, the NMR apparatus may be mounted in the drilling fluid reservoir. In the reservoir of the invention, the NMR apparatus is preferably movable, especially vertically, and desirably is provided with an open ended vertical hollow cylinder, of a non-magnetic material, passing through the magnet and into which drilling fluid may enter. The cylinder is preferably mounted so that the NMR apparatus may be moved between vertically separated locations on the cylinder. The NMR apparatus is preferably arranged to communicate with a computer as described earlier for the apparatus of the invention.

The apparatus of the invention may further comprise a fluid handling apparatus. The fluid handling apparatus preferably comprises means to mix the drilling fluid, feed lines connected to supplies of fluid components and optionally a holding or mixing tank. When the fluid handling apparatus comprises a mixing tank it is preferably fluidly connected to the drilling fluid reservoir. If the fluid handling apparatus does not comprise a mixing tank, the feed lines are preferably fluidly connected to the drilling fluid reservoir. The mixing means may be present in the mixing tank and/or the drilling fluid reservoir. The fluid handling apparatus also preferably comprises filtering apparatus, e.g. shakers.

Embodiments of the invention will now be described further with reference to the following non-limiting Examples and the accompanying drawings, in which.

Figure 1:
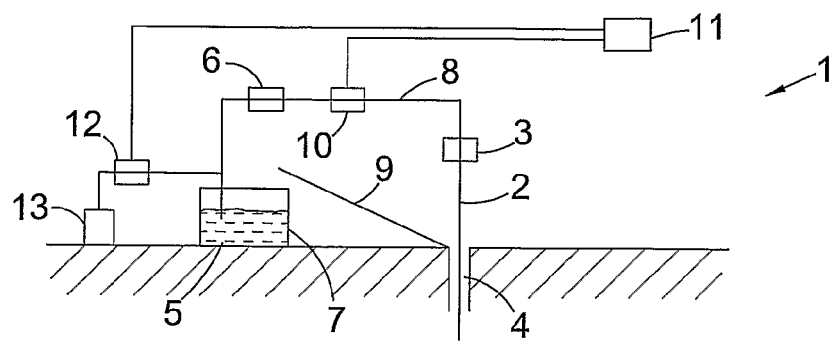
FIG. 1 is a schematic drawing of a well head equipped with the apparatus of the invention.

Referring to FIG. 1 there is shown a well head 1 having a drill string 2, powered by power unit 3, extending down borehole 4. Drilling fluid 5 is pumped by pump 6 from reservoir 7 down flowline 8 to the drill string. Drilling fluid from the distal end of borehole 4 is returned to reservoir 7 through flowline 9. Drilling fluid flowing through flowline 8 is analysed by an apparatus 10 according to the invention the signals from which are passed to computer 11. Where the measured physiochemical properties of the drilling fluid are found to be outside the pre-set target range, computer 11 activates pump 12 to transfer an appropriate quantity of an appropriate drilling fluid component from storage tank 13 into reservoir 7.

Figure 2:
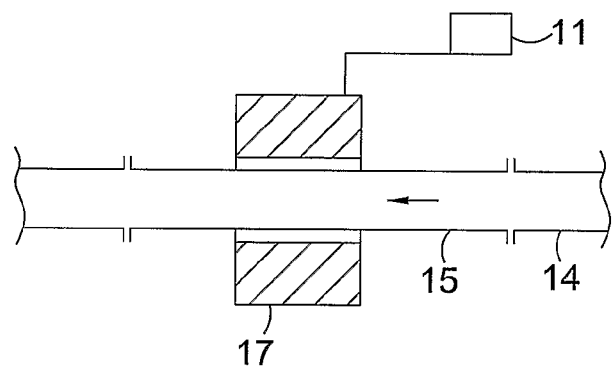
FIGS. 2 to 5 are schematic drawings of four embodiments of the apparatus of the invention.

Referring to FIG. 2, there is shown a drilling fluid flowline 14, a section 15 of which is of non-magnetic material. About section 15 is disposed an NMR apparatus 17, with a cylindrical magnet, which is connected to remote computer 11.

Figure 3:
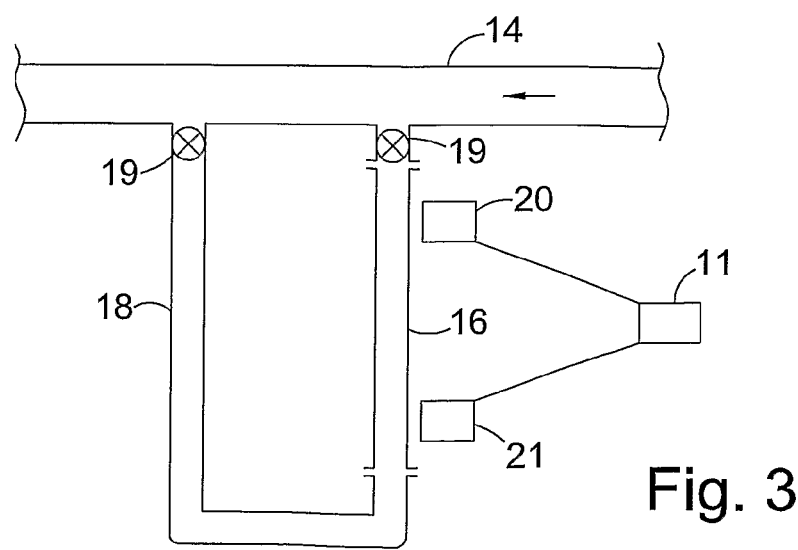

Referring to FIG. 3, there is shown a drilling fluid flowline 14 having a by-pass line 18 provided with valves 19 and vertical non-magnetic material section 16. At two positions along section 16 are disposed two NMR apparatuses 20 and 21, e.g. with horseshoe magnets. The NMR apparatuses are connected to remote computer 11.

Figure 4:
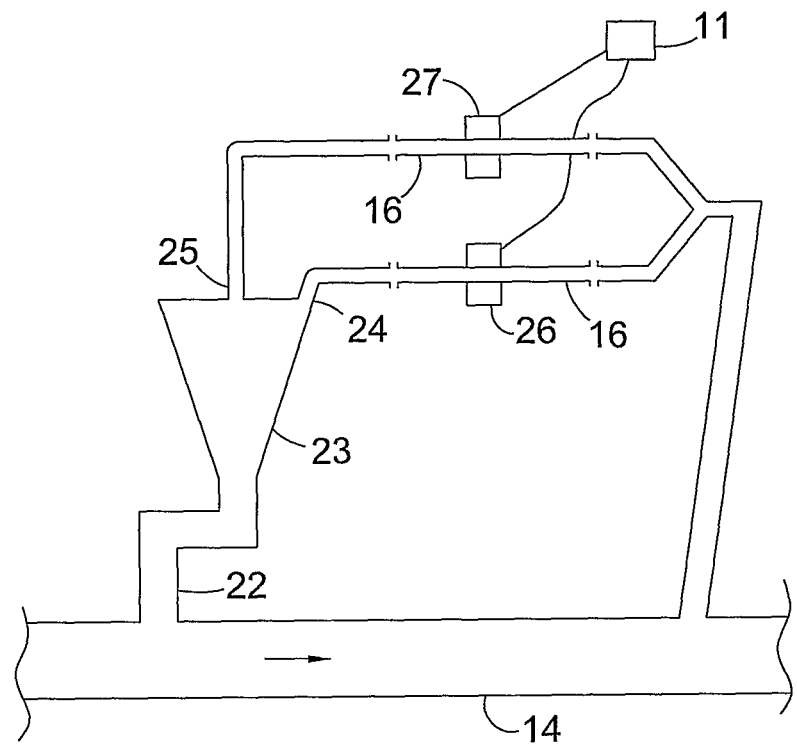

Referring to FIG. 4, there is shown a drilling fluid flowline 14 having a by-pass line 22. In line 22 is disposed a cyclone 23 with two outlets 24, 25 one axial and the other peripheral. The by-pass lines from these outlets each have a non-magnetic material section 16 about each of which is disposed an NMR apparatus 26, 27. The NMR apparatuses are connected to a remote computer 11.

Figure 5:
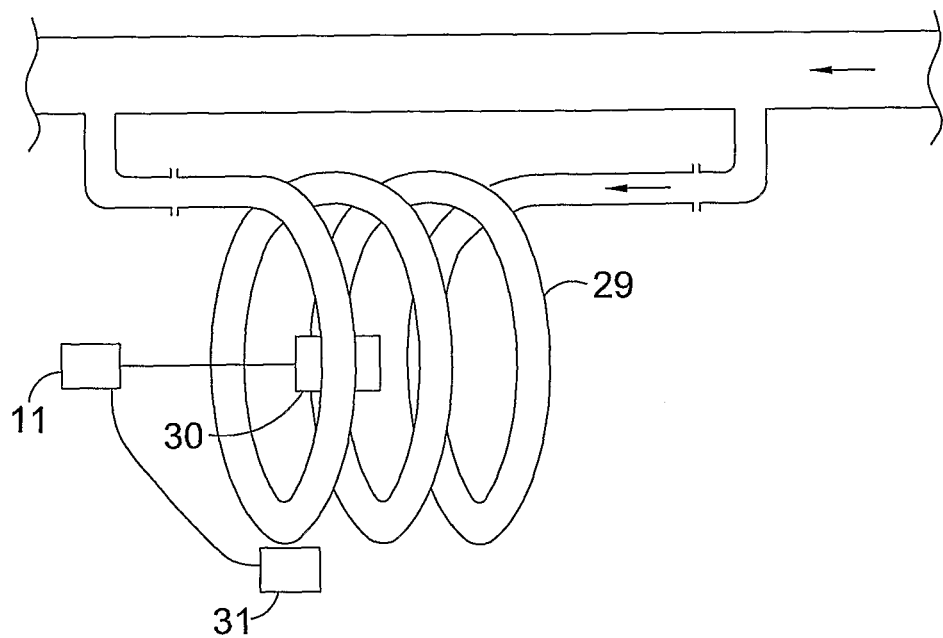

Referring to FIG. 5, there is shown a drilling fluid flowline 14 having a by-pass line 28 having a helical non-magnetic material section 29. At the downstream end of section 29, one horseshoe NMR apparatus 30 is disposed adjacent the section within the helix and a second horseshoe NMR apparatus 31 is disposed adjacent the section but outside the helix.

Figure 6:
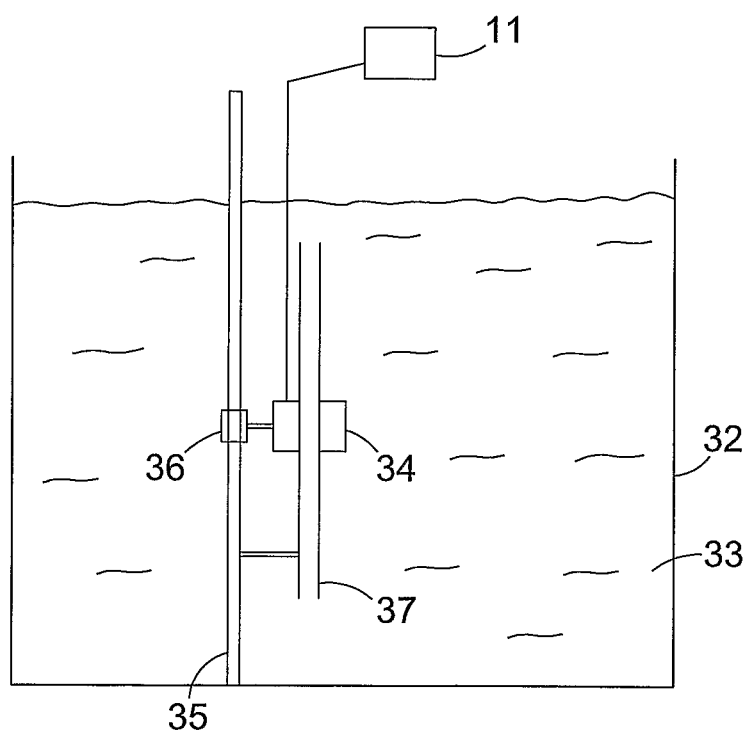
FIG. 6 is a schematic drawing of a reservoir according to the invention.

Referring to FIG. 6, there is shown a drilling fluid reservoir 32 containing drilling fluid 33. Within the fluid a cylindrical magnet NMR apparatus 34 is attached to a vertical support 35 with a driver 36 to drive the apparatus up or down the support. The cylinder magnet of the apparatus is open to allow drilling fluid into the magnet cavity. An open ended tube 37 of non-magnetic material, fixed relative to support 35 but removable if desired, is disposed through the magnet cavity. The NMR apparatus is connected to a remote computer 11.

EXAMPLE 1

NMR Characteristics of Drilling Fluids

Two oil-based drilling fluids, one fresh the other aged, had their oil contents diluted from 85 to 80%, 75% and 70% (in each case % is % wt relative to total water and oil content).

Figure 7:
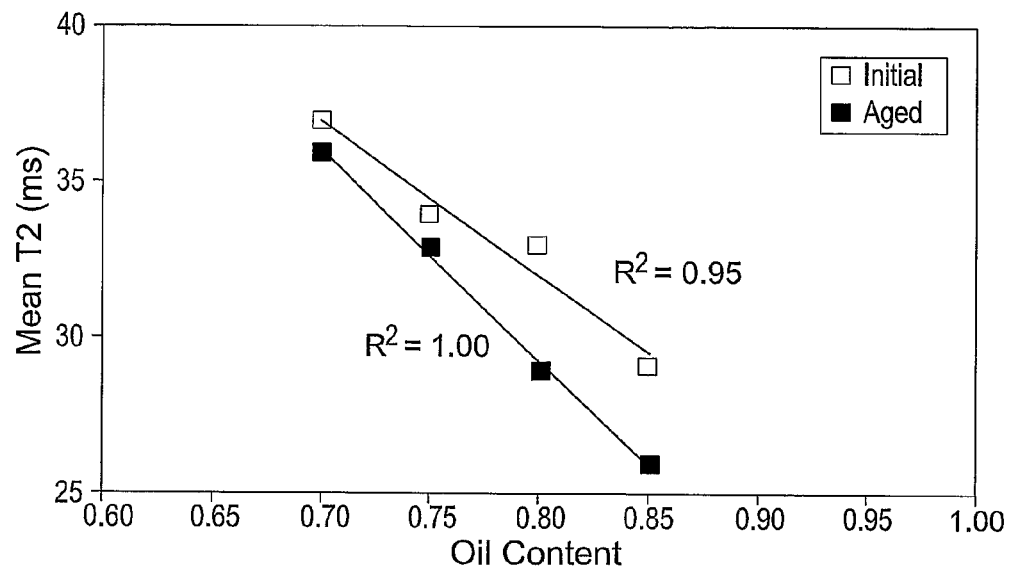
FIG. 7 is a graph showing dependence of $T_2$ on oil content of fresh and aged drilling fluids.

Using a 2 MHz NMR apparatus, the mean value for proton relaxation time $T_2$ was measured. System specifications of the spectrometer were as follows:
Spectrometer frequency: 2.12 MHz
90° pulse length 15.45 µs
180° pulse length 30.9 µs NMR measurements were performed using a MARAN Ultra-bench top NMR spectrometer. The samples (20 ml) were placed in tubes and thermostated to 35° C. in an oven. $T_2$ relaxation measurements were performed using a CPMG pulsed sequence. The application parameters for the experiment are shown below.
Pulse sequence: CPMG
Number of scans: 24
Relaxation delay: 10 s
Number of echoes: 5120
90-180° interecho spacing: 700 µs The results, shown in FIG. 7, demonstrate that $T_2$ correlates well with oil content.

EXAMPLE 2

NMR Characteristics of Drilling Fluids

Figure 8:
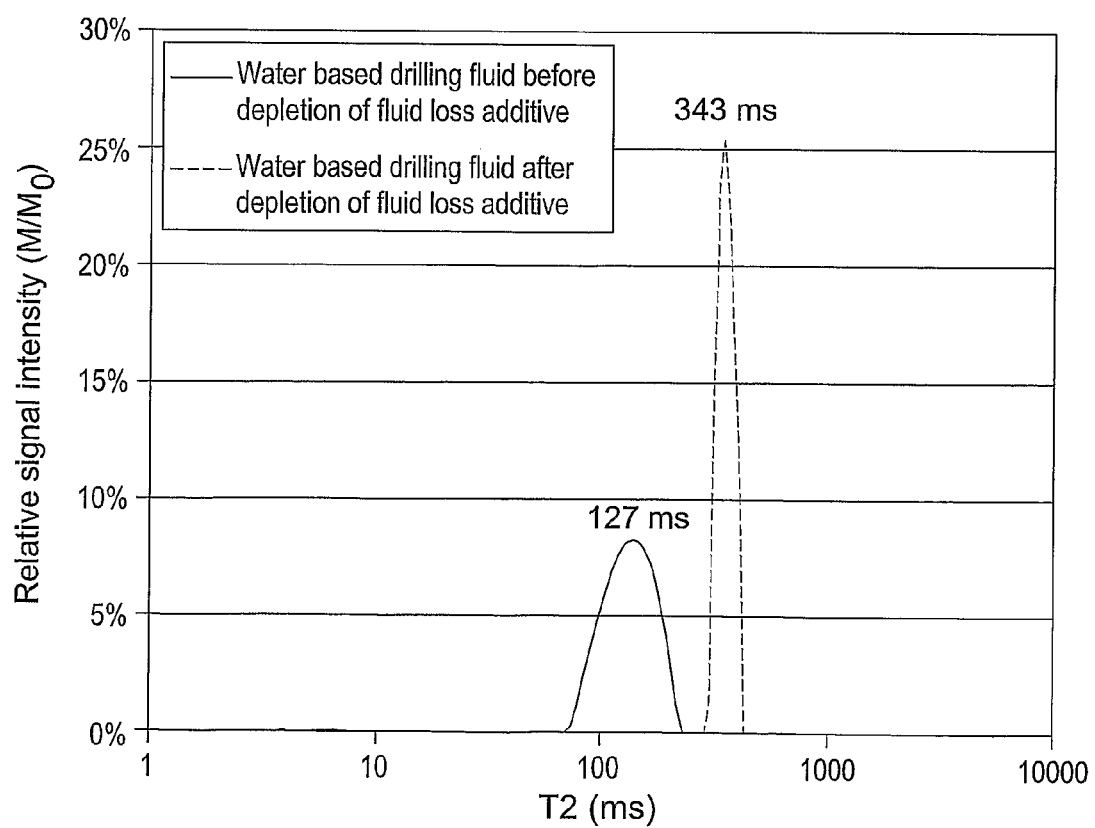
FIG. 8 is a graph showing the dependence of NMR signal amplitude and relaxation time $T_2$ before and after depletion of a fluid loss additive in a water-based drilling fluid.

To simulate the depletion of fluid loss control agent, two water-based drilling fluid samples were analysed using NMR, one sample had a fluid loss control agent added while the other did not. Using a 10 MHz NMR apparatus, proton relaxation time $T_2$ was measured and the signal decay was converted by a computer to a $T_2$ relaxation time distribution. The shift in relaxation time distribution for the fluid samples with and without the fluid loss additive quantifies the effect of the depletion of the fluid loss additive on mean $T_2$ relaxation time and the shape of the distributions. The results are shown in FIG. 8.

EXAMPLE 3

NMR Characteristics of Drilling Fluids

Two oil-based drilling fluid samples with different sensitivity to sagging of the weighting material were analysed by NMR using a 1D profile experiment. Samples (20 ml) were aged statically in an oven at a temperature of 65° C. for 5 days. After aging, the samples were reconditioned to 35° C. before they were introduced into the NMR apparatus.

Using a 2 MHz NMR apparatus (with the system specification as described for example 1) with a gradient coil, the locally resolved signal amplitude of the proton relaxation time $T_2$ was recorded along the sample height.

A PROFILE pulse sequence was used. The application parameters are listed below:
Number of scans: 12
Relaxation delay: 10 s
Pre gradient pulse length: 100 µs
Gradient pulse length: 2000 µs
Pre acquisition settle length: 1000 µs
90-180° interecho spacing: 4000 µs
Gradient amplitude: 300

Figure 9:
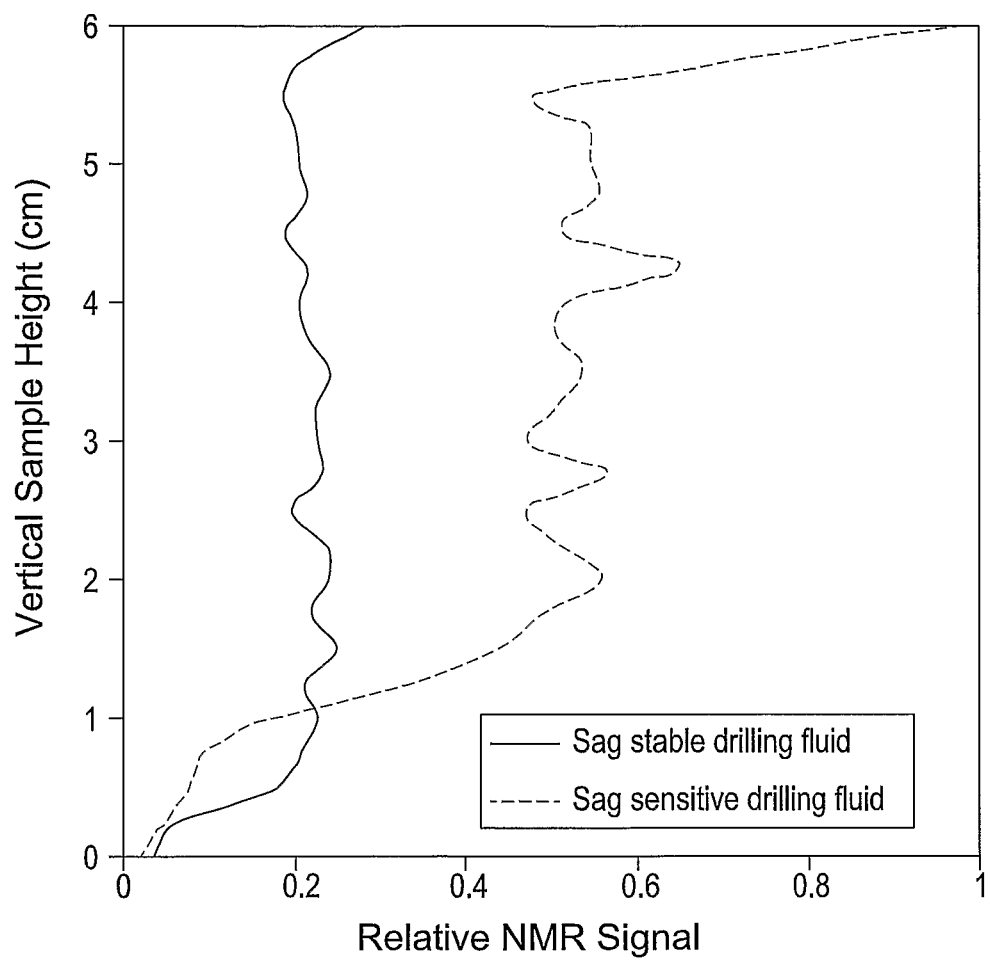
FIG. 9 is a graph showing locally resolved NMR signal intensity along the height of two fluid samples, one that is sensitive to sagging and one that is less sensitive to sagging.

The sample that is more stable to sagging and the sample that is more sensitive to sagging can clearly be distinguished as can be seen from FIG. 9.

The invention claimed is:

1. A method of determining a physiochemical property of a drilling fluid at a drilling site during a drilling phase and controlling the physiochemical properties of the drilling fluid, said method comprising
    detecting a nuclear magnetic resonance signal from out-of-hole drilling fluid at said site;
    calculating from said nuclear magnetic resonance signal a value indicative of said physiochemical property of said drilling fluid;
    comparing the determined properties with pre-set target values for said properties; and
    modifying the drilling fluid to adjust said properties towards said target values, wherein said drilling fluid is recirculated during said drilling phase.

2. A method as claimed in claim 1, wherein said nuclear magnetic resonance signal is detected from drilling fluid passing from a borehole to a drilling fluid reservoir, from drilling fluid in the drilling fluid reservoir, from drilling fluid passing from the drilling fluid reservoir to the borehole, or from a sample extracted from said passing fluid or the drilling fluid reservoir.

3. A method as claimed in claim 1, wherein said nuclear magnetic resonance signal detected is a hydrogen ($^1$H) proton spin relaxation time, a signal amplitude or intensity, a translational diffusion coefficient, a chemical shift or a peak broadening.

4. A method as claimed in claim 3, wherein said nuclear magnetic resonance signal detected is a hydrogen ($^1$H) proton spin relaxation time.

5. A method as claimed in claim 1, wherein the step of detecting a nuclear magnetic resonance signal is carried out at regular intervals during the drilling phase.

6. A method as claimed in claim 1, wherein said drilling fluid property is time invariant.

7. A method as claimed in claim 1, wherein said drilling fluid property is time variant.

8. A method as claimed in claim 1, wherein said drilling fluid property is selected from the group consisting of:
    Viscosity,
    Density,
    Fluid loss control,
    Acidity,
    $H_2S$ content,
    Solids content,
    Gel strength,
    Time to build up gel strength,
    Emulsion droplet size,
    Emulsion stability,
    Particle and fluid segregation processes (sag),
    Oil:water ratio,
    Oil:brine ratio,
    Oil content,
    Water content,
    Brine content, Dissolved gas content, and
Glycol content.

9. A method as claimed in claim 8, wherein the drilling fluid property is selected from the group consisting of:
Oil:water ratio,
oil:brine ratio,
Emulsion droplet size,
Time to build up gel strength,
Particle and fluids segregation processes (sag), and
Dissolved gas content.

10. A method as claimed in claim 1, wherein said nuclear magnetic resonance signal is detected by at least two NMR measurement techniques.

11. A method as claimed in claim 1, wherein the step of calculating a value indicative of said property comprises comparing the measured nuclear magnetic resonance signal to a signal obtained from standards.

12. A method as claimed in claim 1, wherein the step of modifying the drilling fluid is carried out during the drilling phase.

13. A method or process as claimed in claim 1, which is automated.

14. The method of claim 1, wherein the nuclear magnetic resonance signal is detected after the drilling fluid has left the borehole.

15. Apparatus for determining properties of out-of-hole drilling fluid, said apparatus comprising:
a drilling fluid flow tube mounted on a flow tube connecting a drilling fluid reservoir and a drill string or drilling fluid discharge site, the walls of at least a portion of said tube being of a non-magnetic material;
disposed at said portion, a nuclear magnetic resonance apparatus; and
a computer arranged to receive signals from said apparatus indicative of nuclear magnetic resonance parameters of fluid in said tube and to calculate from said nuclear magnetic resonance parameters values for said properties of said out-of-hole drilling fluid, wherein said flow tube is shaped to impose a centrifugal force on fluid flowing therethrough and wherein said nuclear magnetic resonance apparatus is disposed or disposable to detect signals weighted by relatively dense or by relatively less dense components in said fluid.

16. Apparatus as claimed in claim 15 wherein said flow tube is provided with a valve operable to stop fluid flow therethrough and wherein said nuclear magnetic resonance apparatus is vertically displaceable relative to said flow tube.

17. Apparatus as claimed in claim 15, wherein said drilling fluid flow tube mounted on a flow tube connecting a drilling fluid reservoir and a drill string or drilling discharge site is valved to stop fluid flow therethrough.

18. The method of claim 1, wherein the nuclear magnetic resonance signal is detected before the drilling fluid enters the borehole.

19. Apparatus for determining properties of out-of-hole drilling fluid, said apparatus comprising:
a drilling fluid flow tube mounted on a flow tube connecting a drilling fluid reservoir and a drill string or drilling fluid discharge site, the walls of at least a portion of said tube being of a non-magnetic material;
disposed at said portion, a nuclear magnetic resonance apparatus; and
a computer arranged to receive signals from said apparatus indicative of nuclear magnetic resonance parameters of fluid in said tube and to calculate from said nuclear magnetic resonance parameters values for said properties of said out-of-hole drilling fluid, wherein said flow tube comprises a helical section and wherein a first nuclear magnetic resonance apparatus is disposed within the central cavity of said helical section and a second nuclear magnetic resonance apparatus is disposed externally of said helical section.

20. Apparatus as claimed in claim 19, wherein said flow tube is provided with a valve operable to stop fluid flow therethrough and wherein said nuclear magnetic resonance apparatus is vertically displaceable relative to said flow tube.

21. Apparatus as claimed in claim 19, wherein said drilling fluid flow tube mounted on a flow tube connecting a drilling fluid reservoir and a drill string or drilling discharge site is valved to stop fluid flow therethrough.

22. Apparatus for determining properties of out-of-hole drilling fluid, said apparatus comprising:
a drilling fluid flow tube mounted on a flow tube connecting a drilling fluid reservoir and a drill string or drilling fluid discharge site, the walls of at least a portion of said tube being of a non-magnetic material;
disposed at said portion, a nuclear magnetic resonance apparatus; and
a computer arranged to receive signals from said apparatus indicative of nuclear magnetic resonance parameters of fluid in said tube and to calculate from said nuclear magnetic resonance parameters values for said properties of said out-of-hole drilling fluid, wherein said flow tube comprises a cyclonic separation section having a first dense component discharge pipe and a second less dense component discharge pipe, and wherein said nuclear magnetic resonance apparatus is disposed or disposable to record signals separately from said first and second pipes.

23. Apparatus as claimed in claim 22, wherein said flow tube is provided with a valve operable to stop fluid flow therethrough and wherein said nuclear magnetic resonance apparatus is vertically displaceable relative to said flow tube.

24. Apparatus as claimed in claim 22, wherein said drilling fluid flow tube mounted on a flow tube connecting a drilling fluid reservoir and a drill string or drilling discharge site is valved to stop fluid flow therethrough.

* * * * *